United States Patent [19]

Kim

[11] Patent Number: 5,182,394

[45] Date of Patent: Jan. 26, 1993

[54] LIQUID CRYSTALLINE DIGLYCIDYL COMPOUNDS

[75] Inventor: Ki-Soo Kim, Katonah, N.Y.

[73] Assignee: Akzo N.V., Arnhem, Netherlands

[21] Appl. No.: 820,187

[22] Filed: Jan. 14, 1992

[51] Int. Cl.$^5$ .......................................... C07D 303/16
[52] U.S. Cl. .................................. 549/557; 525/539
[58] Field of Search ....................................... 549/557

[56] References Cited

U.S. PATENT DOCUMENTS

| | | | |
|---|---|---|---|
| 3,067,171 | 12/1962 | Hoppe | 549/557 |
| 3,316,277 | 4/1967 | Frank et al. | 260/348 |
| 3,395,118 | 7/1968 | Reinking et al. | 549/557 |
| 4,638,073 | 1/1987 | Walba et al. | 549/557 |
| 4,764,581 | 8/1988 | Muller et al. | 549/557 |
| 4,835,295 | 5/1989 | Walba et al. | 549/557 |

FOREIGN PATENT DOCUMENTS 1222076  8/1966  Fed. Rep. of Germany ...... 549/557

*Primary Examiner*—Joseph E. Evans
*Attorney, Agent, or Firm*—Richard P. Fennelly; Louis A. Morris

[57] ABSTRACT

The liquid crystalline compounds of the structure

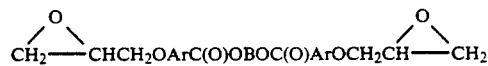

where Ar represents phenylene (e.g., bonded in their para positions) and B represents a cyclohydrocarbylene bridging group such as cyclohexylene or phenylene, are disclosed.

3 Claims, No Drawings

LIQUID CRYSTALLINE DIGLYCIDYL COMPOUNDS

BACKGROUND OF THE INVENTION

It is known to form liquid crystalline diglycidyl compounds. For example, U.S. Pat. No. 4,764,581 to H. P. Muller et al. shows diglycidyl compounds of optionally ring-substituted 4-hydroxy-phenyl 4-hydroxybenzoates.

There is also a disclosure in Organic Coatings and Plastics Chemistry, Volume 40 (American Chemical Society), pp. 899–902 of certain epoxy resins from alkylene-bis-(p-hydroxybenzoate). The alkylene group is specified as being an acyclic unit having anywhere from two to six carbon atoms in the linear hydrocarbon chain.

SUMMARY OF THE INVENTION

The present invention relates to liquid crystalline compounds which are the diglycidyl ether of a 1,4-bis(p-hydroxybenzoyloxy) cyclohydrocarbon. Representative cyclohydrocarbon moieties in such compounds are phenylene and cyclohexylene structures.

DETAILED DESCRIPTION OF THE INVENTION

The liquid crystalline compounds of the present invention have the structure

where Ar represents phenylene (e.g., bonded in their para positions) and B represents a cyclohydrocarbylene bridging group such as cyclohexylene or phenylene.

The above-referenced compounds can be advantageously synthesized by reacting epichlorohydrin, for example, with the selected 1,4-bis(p-hydroxybenzoyloxy) cyclohydrocarbon in the presence of a suitable tetraalkylammonium halide catalyst amine acid acceptor. Illustrative, more detailed procedures for making the cis- and trans-cyclohexane compounds is given in Examples 1 and 2 below.

The compounds described herein have been found useful as a processing and stabilizing agent for the melt spinning of polyolefin ketone compositions as more fully described in U.S. Ser. No. 820,186, filed on even date herewith.

The present invention is further illustrated by the Examples which follow.

EXAMPLE 1

This illustrates formation of the diglycidyl ether of 1,4-bis(p-hydroxybenzoyloxy) cyclohexane.

A mixture of 15.6 g (0.04 mole) of 1,4-bis(p-hydroxybenzoyloxy) cyclohexane, cis form, epichlorohydrin (55 g, 0.59 mole) and tetraethylammonium chloride (0.08 g) was heated at 80° C. overnight. The reaction mixture was then cooled to about 60° C. and 9 g of 50% aqueous sodium hydroxide was added while applying low vacuum to remove water. The reaction mixture was heated for three additional hours, sodium chloride was filtered off, and excess epichlorohydrin was recrystallized from an acetonitrile/methanol mixture. The melting point of the product was 137° C., and the yield was 17.5 g (88%).

EXAMPLE 2

The same reaction performed in Example 1 was used to synthesize the trans form of the cyclohexane-containing compound. It had a melting point of 205° C., and the yield was 80%.

The foregoing Examples are intended to set forth certain illustrative embodiments of the present invention and should, therefore, not be construed in a limiting sense. The scope of protection sought is set forth in the claims which follow.

I claim:

1. A liquid crystalline compound which is the diglycidyl ether of a 1,4-bis (p-hydroxybenzoyloxy) cyclohexane.

2. A compound as claimed in claim 1 wherein the compound is in the trans form.

3. A compound as claimed in claim 1 wherein the compound is in the cis form.